United States Patent
DiIanni et al.

(10) Patent No.: US 10,124,112 B2
(45) Date of Patent: Nov. 13, 2018

(54) FLUID DELIVERY DEVICE AND TRANSCUTANEOUS ACCESS TOOL WITH BLOOD GLUCOSE MONITORING FOR USE THEREWITH

(71) Applicants: Insulet Corporation, Bedford, MA (US); Nova Biomedical Corporation, Waltham, MA (US)

(72) Inventors: Steven DiIanni, Danvers, MA (US); Ian McLaughlin, Boxborough, MA (US); Jason Brian O'Connor, South Boston, MA (US); Robert Campbell, Waltham, MA (US); Kevin Schmid, Boxford, MA (US); Thomas Peterson, Waltham, MA (US)

(73) Assignees: Insulet Corporation, Billerica, MA (US); Nova Biomedical Corporation, Waltham, MA (US)

( * ) Notice: Subject to any disclaimer, the term of this patent is extended or adjusted under 35 U.S.C. 154(b) by 269 days.

(21) Appl. No.: 13/854,463

(22) Filed: Apr. 1, 2013

(65) Prior Publication Data
US 2014/0128839 A1     May 8, 2014

Related U.S. Application Data

(63) Continuation of application No. PCT/US2013/034674, filed on Mar. 29, 2013.
(Continued)

(51) Int. Cl.
*A61M 31/00*     (2006.01)
*A61M 5/145*     (2006.01)
(Continued)

(52) U.S. Cl.
CPC ..... *A61M 5/14566* (2013.01); *A61B 5/14532* (2013.01); *A61B 5/14865* (2013.01);
(Continued)

(58) Field of Classification Search
CPC .............. A61M 5/142; A61M 5/14244; A61M 5/14252; A61M 5/14532; A61M 5/14865;
(Continued)

(56) References Cited

U.S. PATENT DOCUMENTS 5,261,884 A    11/1993   Stern et al.
5,503,628 A    4/1996   Fetters et al.
(Continued)

FOREIGN PATENT DOCUMENTS

EP    2397181 A1   12/2011
EP    2830499      10/2013
(Continued)

OTHER PUBLICATIONS

PCT International Search Report and Written Opinion dated Aug. 6, 2013, received in corresponding PCT Application No. PCT/US13/34674, pp. 1-19.
(Continued)

*Primary Examiner* — Kevin C Sirmons
*Assistant Examiner* — Tiffany Legette-Thompson
(74) *Attorney, Agent, or Firm* — Grossman Tucker Perreault & Pfleger PLLC

(57) ABSTRACT

An infusion device comprising a fluid reservoir for containing a therapeutic fluid; and a transcutaneous access tool fluidly coupled to the fluid reservoir for delivering the therapeutic fluid subcutaneously and for introducing a monitoring test strip subcutaneously, and methods of use thereof.

20 Claims, 17 Drawing Sheets

Related U.S. Application Data

(60) Provisional application No. 61/618,028, filed on Mar. 30, 2012.

(51) Int. Cl.
    *A61B 5/145*     (2006.01)
    *A61B 5/1486*     (2006.01)
    *F04B 9/02*     (2006.01)
    *A61M 5/142*     (2006.01)
    *A61M 5/172*     (2006.01)
    *A61M 5/158*     (2006.01)
    *A61M 5/32*     (2006.01)
    *A61M 5/14*     (2006.01)

(52) U.S. Cl.
    CPC ...... *A61M 5/1452* (2013.01); *A61M 5/14244* (2013.01); *A61M 5/14248* (2013.01); *A61M 5/158* (2013.01); *A61M 5/1723* (2013.01); *F04B 9/02* (2013.01); *A61M 5/3291* (2013.01); *A61M 2005/1403* (2013.01); *A61M 2005/14252* (2013.01); *A61M 2005/14506* (2013.01); *A61M 2230/201* (2013.01); *F04C 2270/041* (2013.01)

(58) Field of Classification Search
    CPC ...... A61M 5/158; A61M 5/168; A61M 5/172; A61M 5/1723; A61M 5/3291; A61M 2005/14252; A61M 2005/14256; A61M 5/1452; A61M 5/14248; A61M 5/14503; A61M 5/1411; A61M 5/1451; A61M 2205/33; A61M 5/14566; F04B 9/02
    USPC .... 604/65, 66, 504, 164.11, 891.1; 600/316, 600/365
    See application file for complete search history.

(56) References Cited

U.S. PATENT DOCUMENTS

| | | | |
|---|---|---|---|
| 7,018,360 B2 | 3/2006 | Flaherty et al. | |
| 7,128,727 B2 | 10/2006 | Flaherty et al. | |
| 7,144,384 B2 | 12/2006 | Gorman et al. | |
| 9,402,950 B2 | 8/2016 | Dilanni et al. | |
| 2002/0032374 A1 | 3/2002 | Holker et al. | |
| 2003/0163097 A1 | 8/2003 | Fleury et al. | |
| 2004/0010207 A1 | 1/2004 | Flaherty et al. | |
| 2004/0064088 A1 | 4/2004 | Gorman et al. | |
| 2004/0092865 A1* | 5/2004 | Flaherty ............ | A61M 5/14276 604/93.01 |
| 2005/0020980 A1 | 1/2005 | Inoue et al. | |
| 2005/0203461 A1 | 9/2005 | Flaherty et al. | |
| 2005/0238507 A1 | 10/2005 | Dilanni et al. | |
| 2006/0155210 A1 | 7/2006 | Beckman et al. | |
| 2006/0178633 A1 | 8/2006 | Garibotto et al. | |
| 2006/0253085 A1 | 11/2006 | Geismar et al. | |
| 2006/0282290 A1 | 12/2006 | Flaherty et al. | |
| 2007/0005018 A1* | 1/2007 | Tekbuchava ........ | A61M 25/003 604/164.01 |
| 2007/0118405 A1 | 5/2007 | Campbell et al. | |
| 2007/0282269 A1 | 12/2007 | Carter et al. | |
| 2008/0004515 A1 | 1/2008 | Jennewine | |
| 2008/0051738 A1 | 2/2008 | Griffin | |
| 2009/0062767 A1* | 3/2009 | Van Antwerp et al. ...... | 604/504 |
| 2009/0198215 A1 | 8/2009 | Chong et al. | |
| 2010/0152658 A1* | 6/2010 | Hanson ............ | A61M 5/14248 604/136 |
| 2011/0054399 A1 | 3/2011 | Chong et al. | |
| 2011/0230833 A1 | 9/2011 | Landman et al. | |
| 2012/0078161 A1 | 3/2012 | Masterson et al. | |
| 2014/0127048 A1 | 5/2014 | Dilanni et al. | |
| 2014/0142508 A1 | 5/2014 | Dilanni et al. | |
| 2017/0128664 A1 | 5/2017 | Dilanni et al. | |

FOREIGN PATENT DOCUMENTS

| | | |
|---|---|---|
| WO | 9856293 A1 | 12/1998 |
| WO | 2008133702 A1 | 11/2008 |
| WO | 2013149186 | 10/2013 |

OTHER PUBLICATIONS

EPO Search Report dated Nov. 11, 2015, received in corresponding Application No. 13768938.6, 7 pgs.
International Preliminary Report on Patentability dated Oct. 9, 2014, issued in PCT Patent Application No. PCT/US2013/034674, 15 pages.
U.S. Office Action dated Mar. 31, 2015, issued in U.S. Appl. No. 13/854,456, 11 pages.
Notice of Allowance dated May 23, 2018, issued in U.S. Appl. No. 13/854,445, 8 pages.
U.S. Office Action dated Sep. 23, 2015, issued in U.S. Appl. No. 13/854,456, 13 pages.
Notice of Allowance dated Mar. 25, 2016, issued in U.S. Appl. No. 13/854,456, 9 pages.
U.S. Office Action dated May 17, 2016, issued in U.S. Appl. No. 13/854,445, 11 pages.
U.S. Office Action dated Oct. 31, 2017, issued in U.S. Appl. No. 13/854,445, 15 pages.
U.S. Office Action dated Jan. 25, 2017, issued in U.S. Appl. No. 13/854,445, 23 pages.

* cited by examiner

FLUID DELIVERY DEVICE AND TRANSCUTANEOUS ACCESS TOOL WITH BLOOD GLUCOSE MONITORING FOR USE THEREWITH

CROSS-REFERENCE TO RELATED APPLICATIONS

This application is a continuation of PCT Application Serial No. PCT/US13/34674 filed Mar. 29, 2013 and claims the benefit of the filing date of U.S. Provisional Application Ser. No. 61/618,028, filed Mar. 30, 2012, the teachings of which are incorporated herein by reference.

TECHNICAL FIELD

The present invention relates to fluid delivery devices for delivering therapeutic liquids to a patient, and more particularly, to an infusion pump for delivering therapeutic liquids to a patient.

BACKGROUND INFORMATION

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump, to improve the comfort to the user, and/or to incorporate continuous glucose monitoring (CGM). These pumps also include fluid driving mechanisms for driving fluid from a reservoir through the transcutaneous access tool. The fluid driving mechanisms may also be improved to facilitate assembly and use of the pump.

SUMMARY

The present disclosure provides various fluid delivery devices to deliver a liquid medicine or other therapeutic fluid to a patient subcutaneously. In certain embodiments the fluid delivery device may comprise an ambulatory insulin infusion device to administer insulin to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, an infusion device may comprise a fluid reservoir for containing a therapeutic fluid; and a transcutaneous access tool fluidly coupled to the fluid reservoir, which may deliver the therapeutic fluid subcutaneously and introduce a monitoring test strip subcutaneously.

In certain embodiments, a method to treat diabetes mellitus may be provided comprising providing an infusion device with integrated monitoring, with the device comprising a fluid reservoir for containing a therapeutic fluid; and a transcutaneous access tool fluidly coupled to the fluid reservoir, which may deliver the therapeutic fluid subcutaneously and introduce a monitoring test strip subcutaneously; delivering the therapeutic fluid subcutaneously with the transcutaneous access tool to a patient, and introducing the monitoring test strip subcutaneously with the transcutaneous access tool to the patient.

BRIEF DESCRIPTION OF THE DRAWINGS

These and other features and advantages will be better understood by reading the following detailed description, taken together with the drawings wherein.

DETAILED DESCRIPTION

Figure 1:
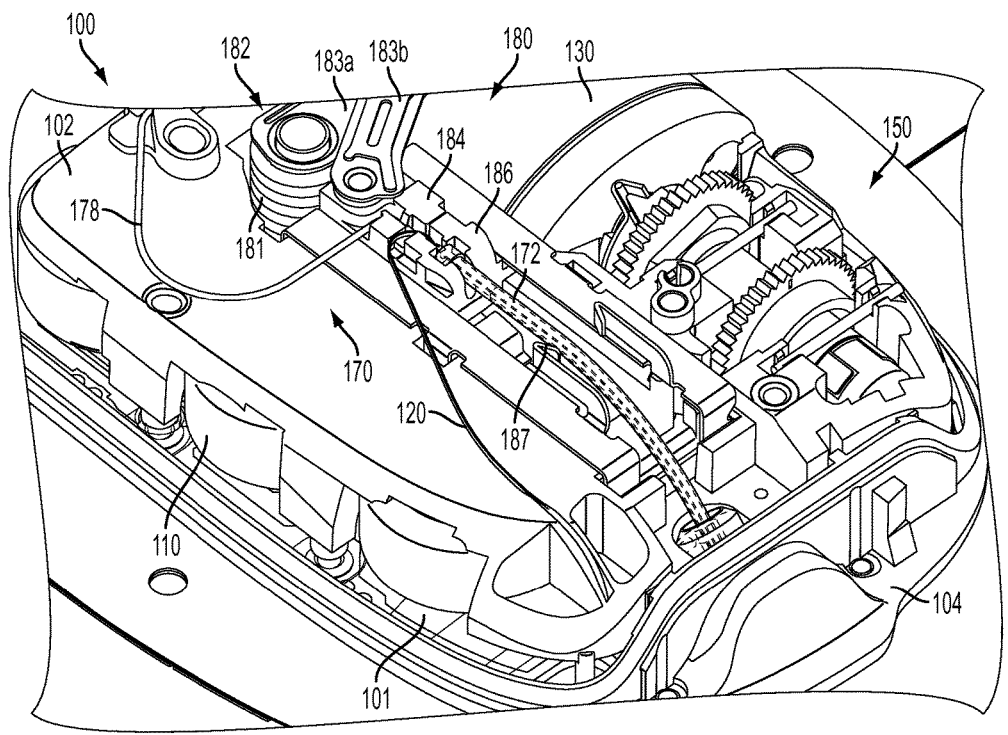
FIG. 1 is a top perspective view of a fluid delivery device with a transcutaneous access tool insertion mechanism in a pre-deployment position, consistent with the present disclosure.
Figure 2:
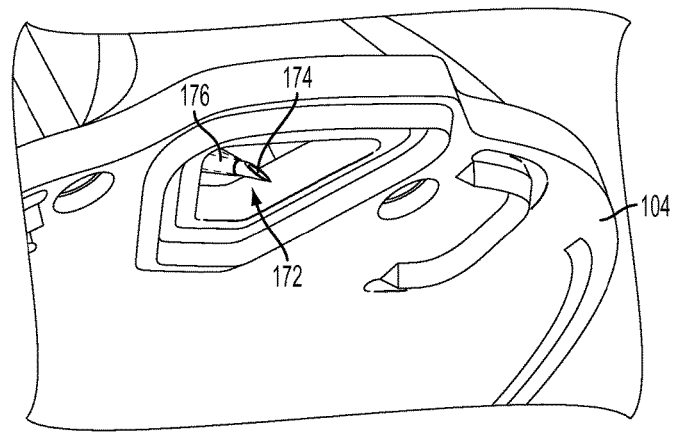
FIG. 2 is a bottom perspective view of a needle and cannula retracted into the fluid delivery device in the pre-deployment position shown in FIG. 1.
Figure 3:
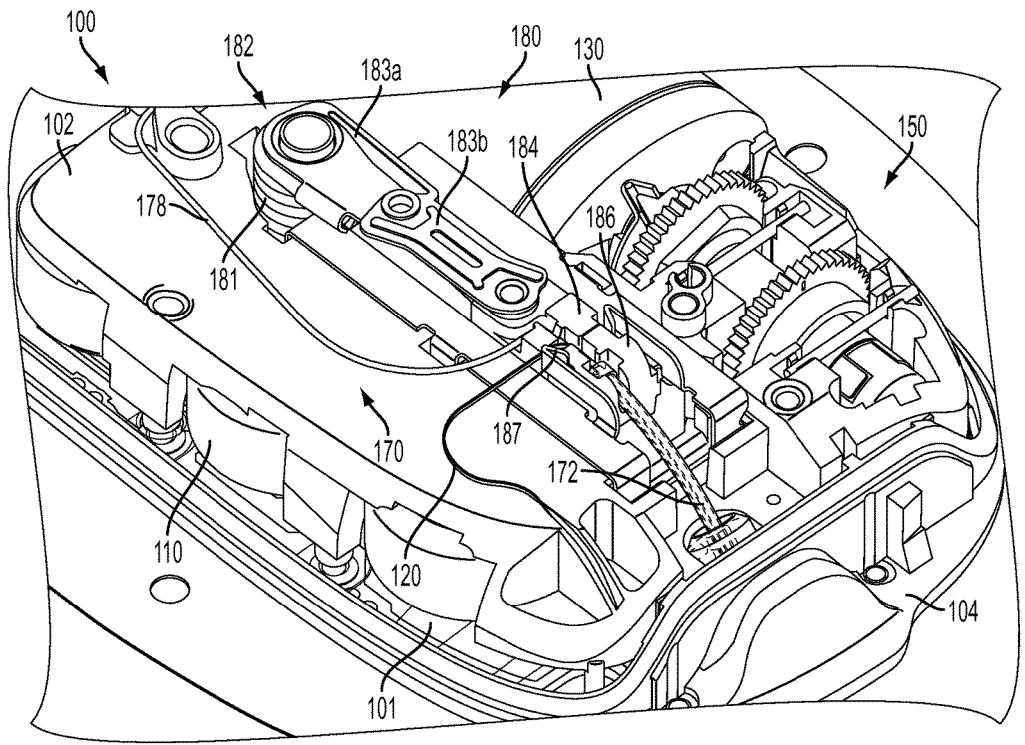
FIG. 3 is a top perspective view of the fluid delivery device shown in FIG. 1 with the insertion mechanism in an intermediate position.
Figure 4:
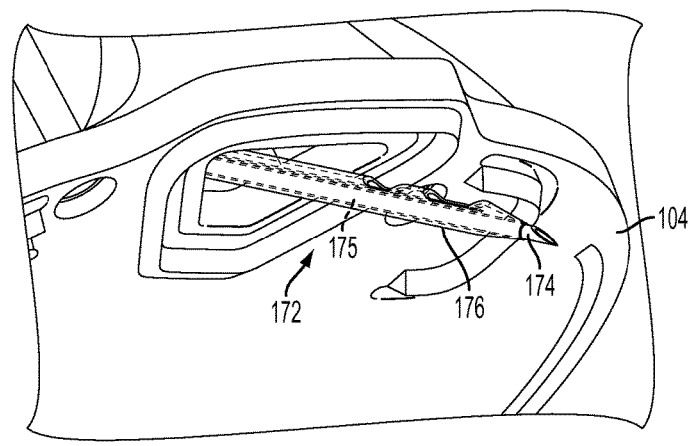
FIG. 4 is a bottom perspective view of the needle and cannula extending from the fluid delivery device in the intermediate position shown in FIG. 3.

A fluid delivery device, consistent with embodiments of the present disclosure, may be used to deliver a therapeutic fluid (e.g. a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory insulin infusion device.

In other embodiments, a fluid delivery device may be used to deliver a therapeutic fluid to a patient with integrated monitoring, such as continuous glucose monitoring (CGM). In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine (e.g. insulin), to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid deliver device 100. The fluid delivery device 100 may also include a housing 104 to enclose the circuit board 101, the chassis 102, and the components 110, 130, 150, 170, 180.

The fluid delivery device 100 may also include integrated monitoring such as continuous glucose monitoring (CGM). A monitor test strip 120 coupled to a monitor (not shown) in the device 100 may be introduced by the transcutaneous access tool 172 subcutaneously. One example of the monitor test strip is a CGM test strip (such as the type available from Nova Biomedical) which may be understood as a glucose sensor configured to test for a concentration level of glucose in the blood of a patient. The fluid delivery device 100 may be configured to receive data from the monitoring test strip concerning a glucose level of the patient, and determining an output of insulin from the reservoir based on the glucose level.

The transcutaneous access tool 172 includes an introducer trocar or needle 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172. The transcutaneous access tool 172 may also be used to introduce a monitoring test strip subcutaneously into the patient for monitoring purposes, as described in greater detail below.

Figure 5:
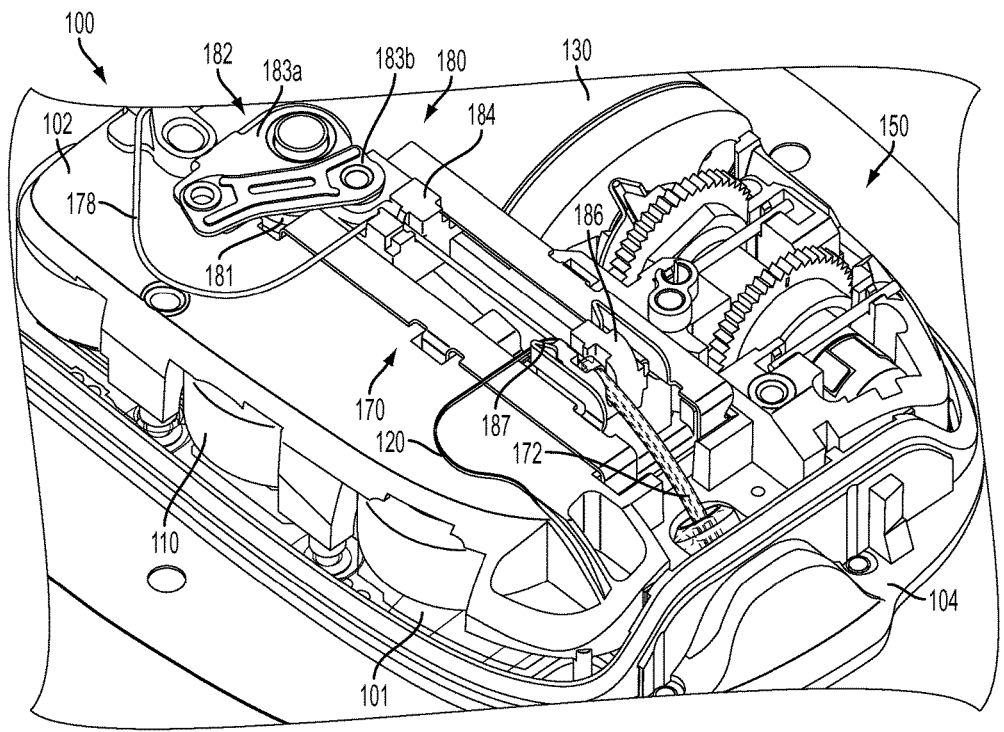
FIG. 5 is a top perspective view of the fluid delivery device shown in FIG. 1 with the insertion mechanism in a post-deployment position.
Figure 6:
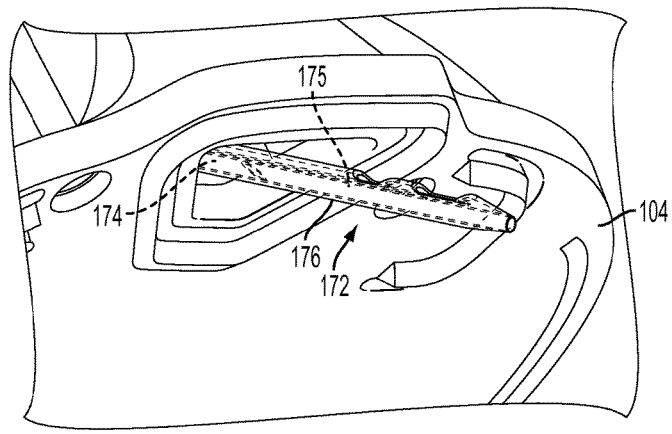
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

One embodiment of the spring-biased linkage mechanism 182 includes a helical torsion spring 181 and first and second linkages 183a, 183b coupled between the torsion spring 181 and the first sliding member 184. Energy stored in the torsion spring 181 applies a force to the linkages 183a, 183b, which applies a force to the first sliding member 184 to move the first sliding member 184 in both the insertion direction and in the retraction direction. In the pre-deployment position (FIG. 1), the torsion spring 181 is loaded and the sliding members 184, 186 are locked and prevented from moving. When the sliding members 184, 186 are released, the energy stored in the torsion spring 181 causes the first linkage 183a to rotate (e.g., clockwise as shown), which applies a force to the first sliding member 184 through the second linkage 183b causing the first sliding member 184 with the needle/trocar 174 to move (with the second sliding member 186) in the insertion direction. In the intermediate position (FIG. 3), the linkages 183a, 183b are fully extended with the needle/trocar 174 and cannula 176 being inserted, the second sliding member 186 is locked, and the remaining energy stored in the torsion spring 181 causes the first linkage 183*a* to continue to rotate, which applies an opposite force to the first sliding member 184 through the second linkage 183*b* causing the first sliding member 184 with the needle/trocar 174 to move in the retraction direction to the post-deployment position (FIG. 5). In the illustrated embodiment, the second sliding member 186 is locked against retraction by one or more latches 187. Thus, in the foregoing manner, the continuous uninterrupted clockwise rotation of first linkage 183*a* via the energy of torsion spring 181 provides the transcutaneous access tool insertion mechanism 180 with the ability to insert and retract the needle/trocar 174 in a single, uninterrupted motion.

The spring-biased linkage mechanism 182 allows a single spring and motion to achieve both the insertion and retraction and has a relatively small size. The spring-biased linkage mechanism 182 also reduces the static stresses caused by locking and holding back the sliding members 184, 186 and provides a smoother and more comfortable needle/trocar insertion because of the way the linkages 183*a*, 183*b* vector the forces applied to the sliding members 184, 186. The static forces on the sliding members 184, 186 are relatively small in the pre-deployment position when the linkages 183*a*, 183*b* are fully retracted. When the deployment starts and the linkages 183*a*, 183*b* start to become extended, the insertion forces increase because the force vectors increase in the insertion direction as the linkages extend 183*a*, 183*b* until a maximum insertion force is reached at the fully extended, intermediate position. By gradually increasing the insertion forces, the needle/trocar insertion and retraction is smoother, quieter and less painful.

Figure 7:
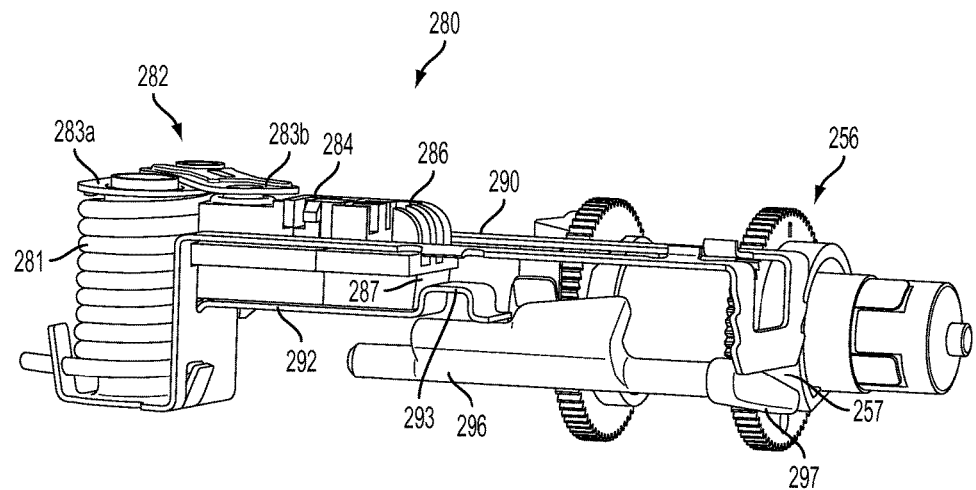
FIG. 7 is a side perspective view of another embodiment of the insertion mechanism, consistent with the present disclosure, in a pre-deployment position.
Figure 8:
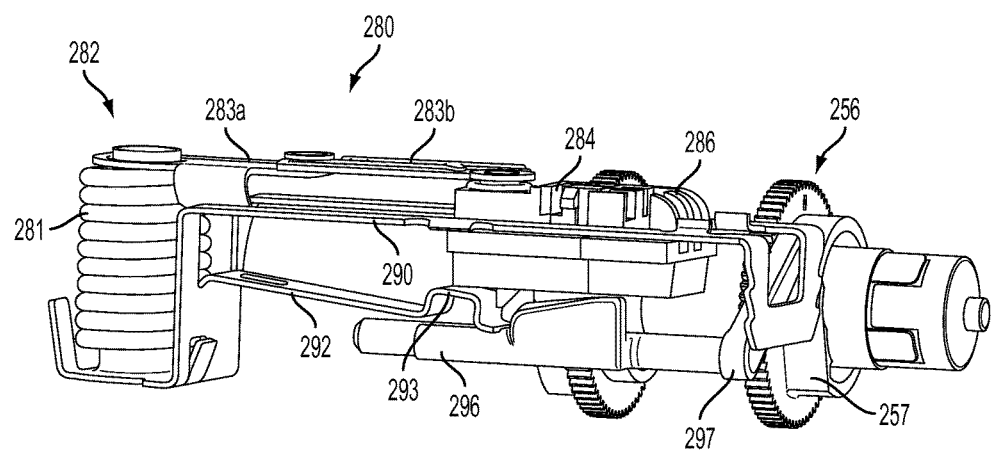
FIG. 8 is a side perspective view of the insertion mechanism shown in FIG. 7 in an intermediate position.

Another embodiment of an insertion mechanism 280 is shown in greater detail in FIGS. 7-10. The sliding members 284, 286 are slidably received in a frame 290 and moved by a spring-biased linkage mechanism 282 including torsion spring 281 and linkages 283*a*, 283*b*. In this embodiment, a cam finger 292 (e.g., extending from the frame 290) engages beneath one or both of the sliding members 284, 286 to lock the sliding members in the retracted or pre-deployment position (FIG. 7). In this pre-deployment position, the cam finger 292 is held against the sliding members 284, 286 by a release bar 296, which may be moved (rotated) to allow the cam finger 292 to move and release the sliding members 284, 286 (FIG. 8). The cam finger 292 may be biased in a downward direction and/or the second sliding member 286 may include a cam surface 287 to help facilitate movement along the cam finger 292 over locking mechanism 293 upon actuation.

The release bar 296 includes a lever 297 for pivoting the release bar 296 between an engaged position against the cam finger 292 (FIG. 7) and a disengaged position releasing the cam finger 292 (FIG. 8). The release bar 296 may be biased toward the disengaged position and held against the cam finger 292 in the engaged position until the lever 297 is released allowing the release bar 296 to move to the disengaged position. In the illustrated embodiment, the lever 297 engages a rotating surface 257 of a drive wheel 256 of the fluid drive mechanism 150 such that the lever 297 is held in the engaged position for part of the rotation and is released at a certain point during the rotation (e.g., when a flat portion of the rotating surface 257 allows the lever 297 to move).

Figure 9:
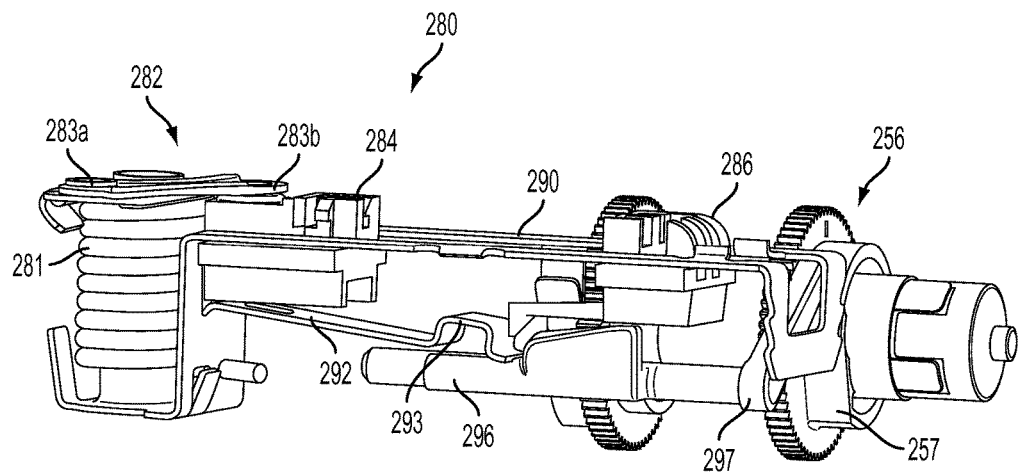
FIG. 9 is a side perspective view of the insertion mechanism shown in FIG. 7 in a post-deployment position.
Figure 10:
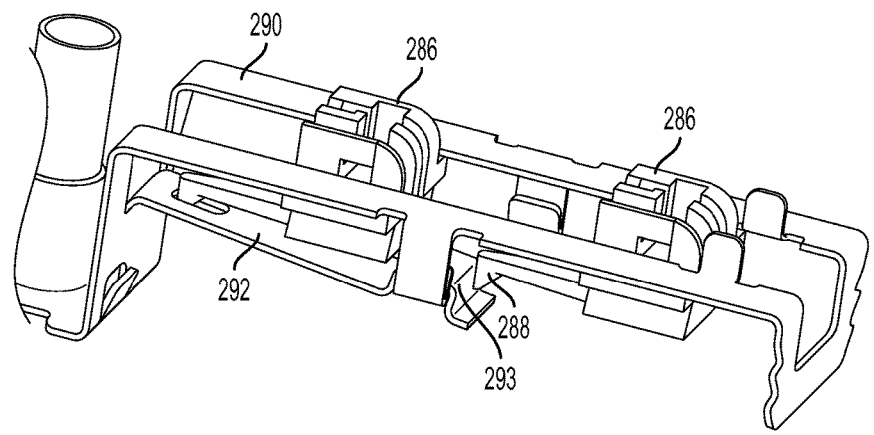
FIG. 10 is a top perspective view of the second sliding member of the insertion mechanism shown in FIG. 7 locked in the pre-deployment and post-deployment positions.
Figure 11:
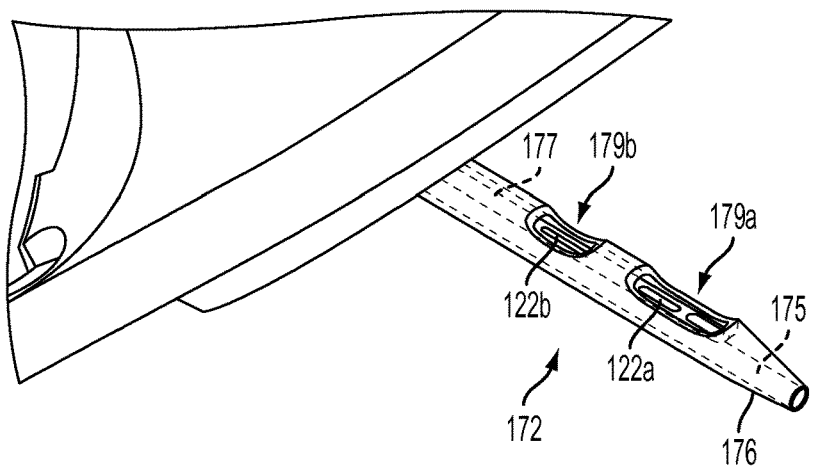
FIGS. 11-17 are views of a bi-lumen cannula used in the fluid delivery device shown in FIGS. 1-6 to insert a monitor test strip transcutaneously.
Figure 12:
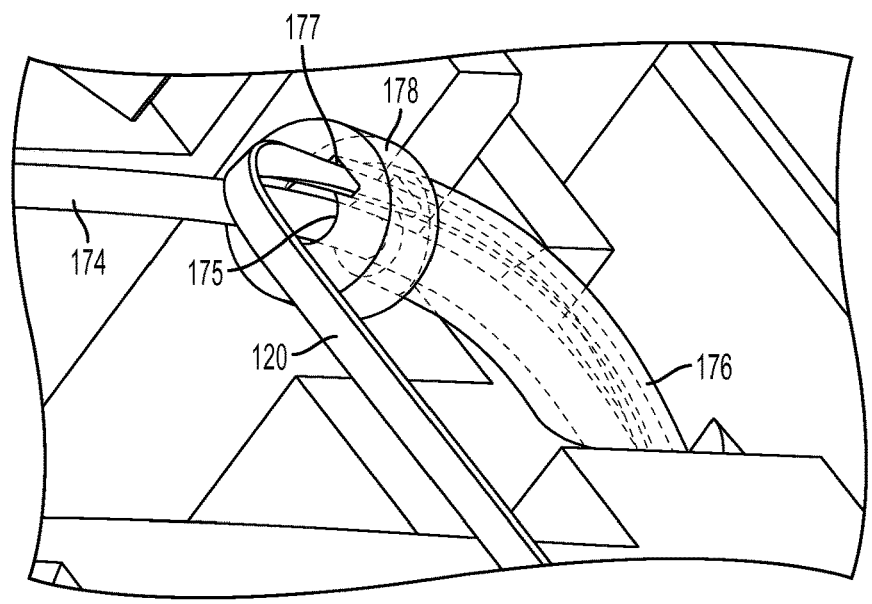
Figure 13:
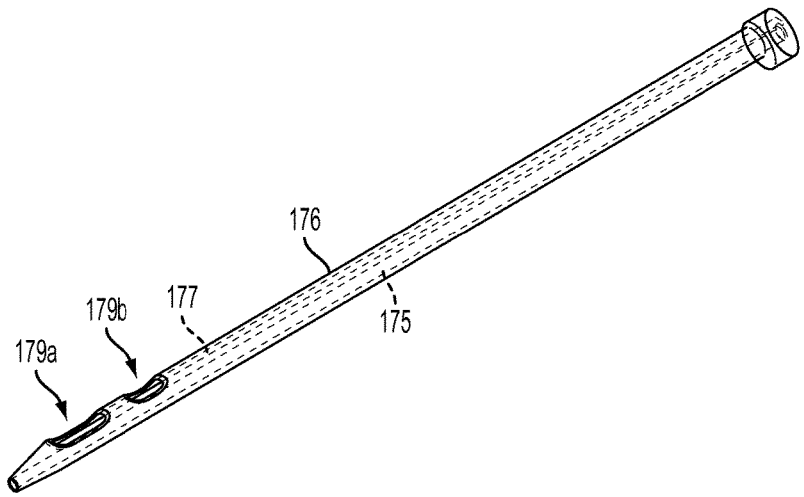
Figure 14:
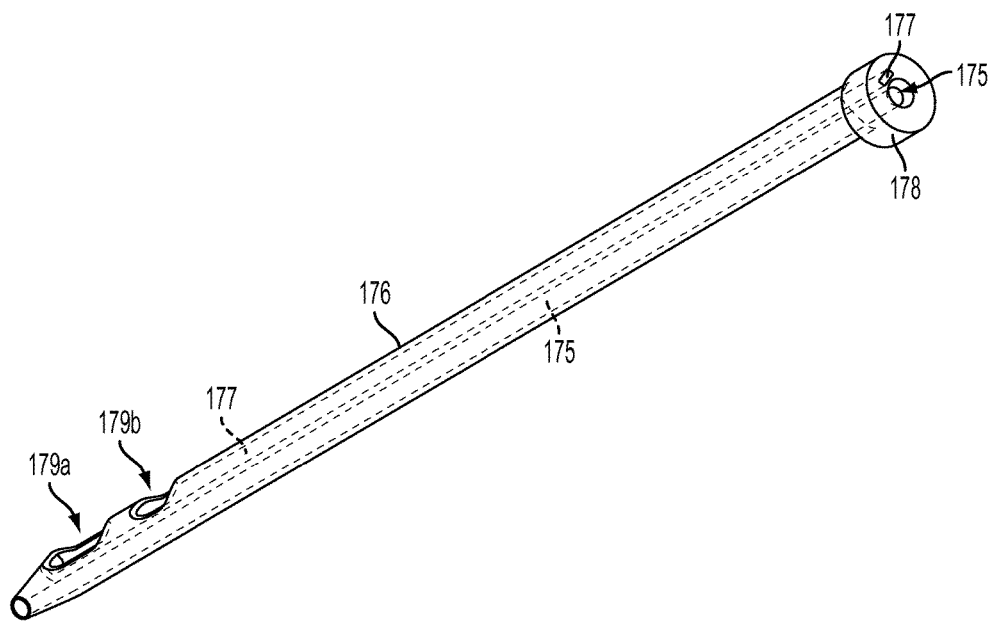
Figure 15:
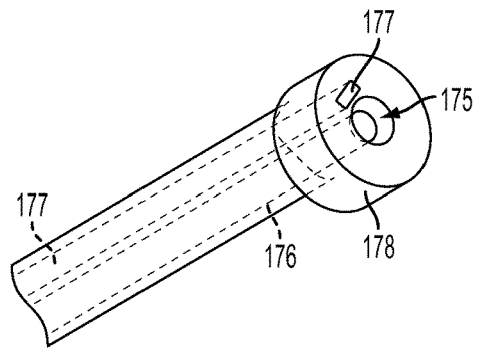
Figure 16:
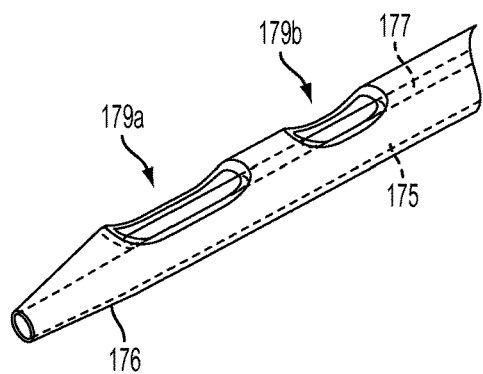
Figure 17:
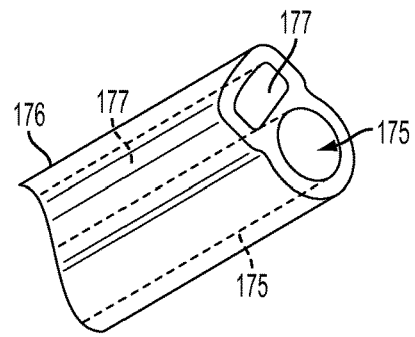
Figure 18:
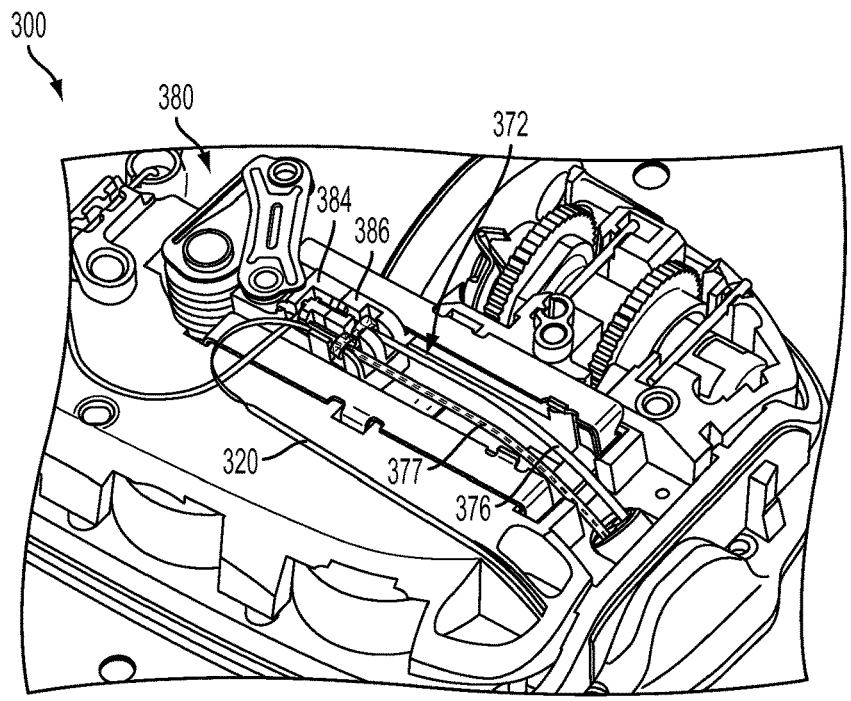
FIGS. 18-23 are views of another embodiment of a fluid delivery device including a cannula with a D-shaped lumen for inserting a monitor test strip transcutaneously.
Figure 19:
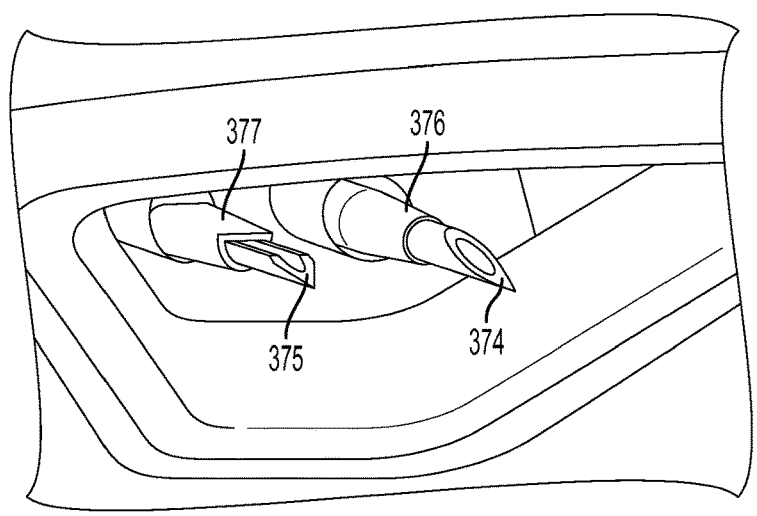
Figure 20:
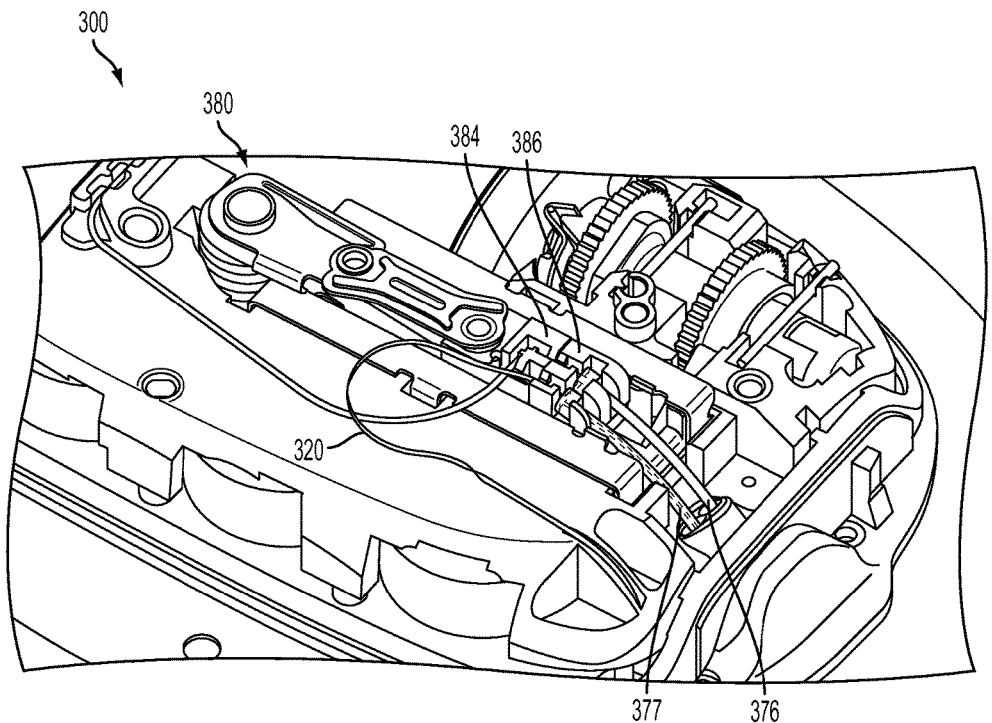
Figure 21:
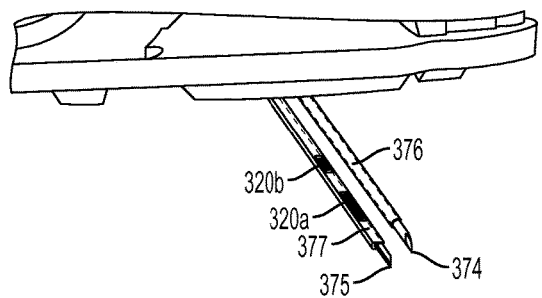
Figure 22:
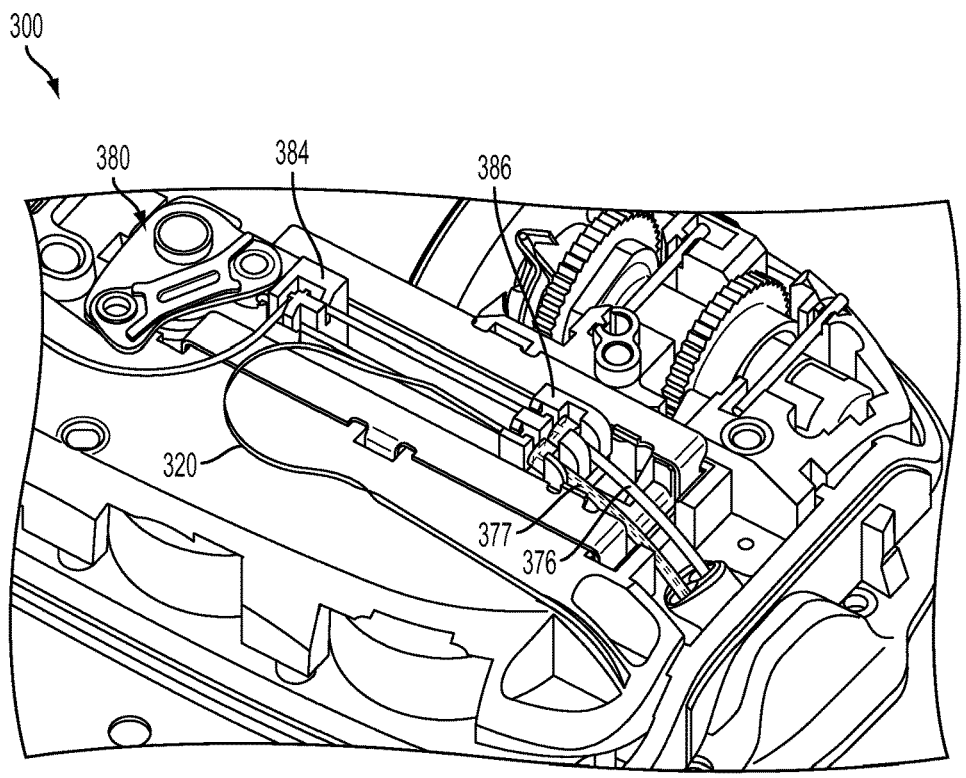
Figure 23:
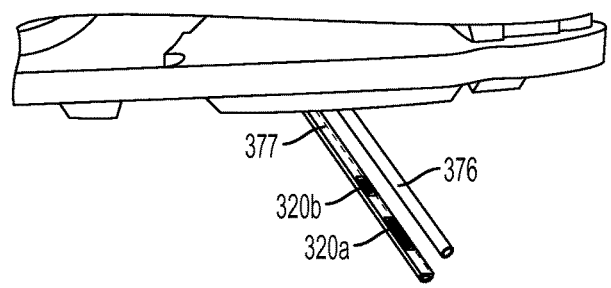
Figure 24:
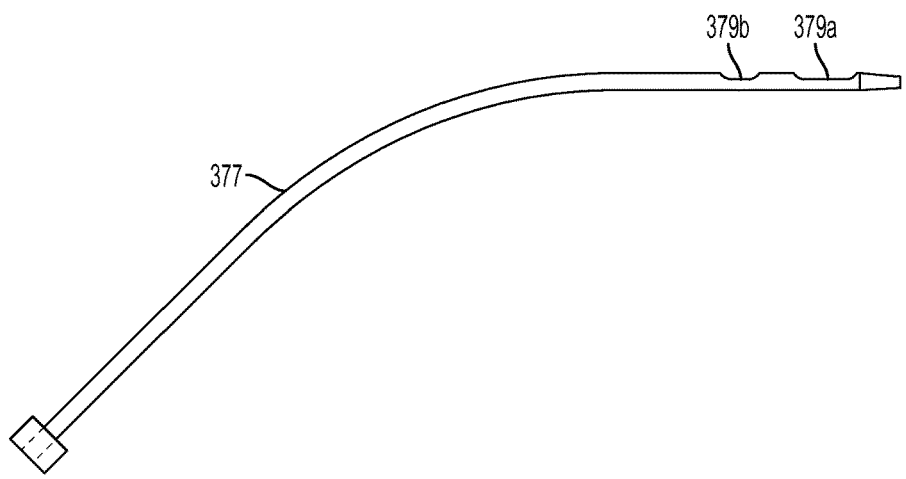
FIGS. 24-26 are views of the D-lumen cannula used in the fluid delivery device of FIGS. 18-23.
Figure 25:
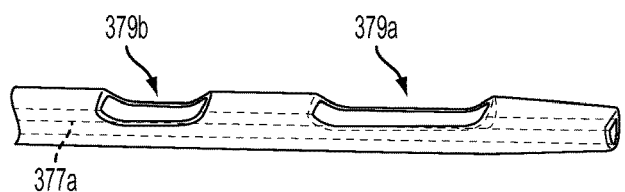
Figure 26:
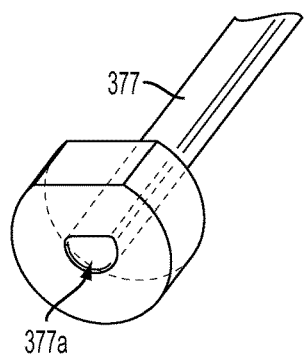
Figure 27:
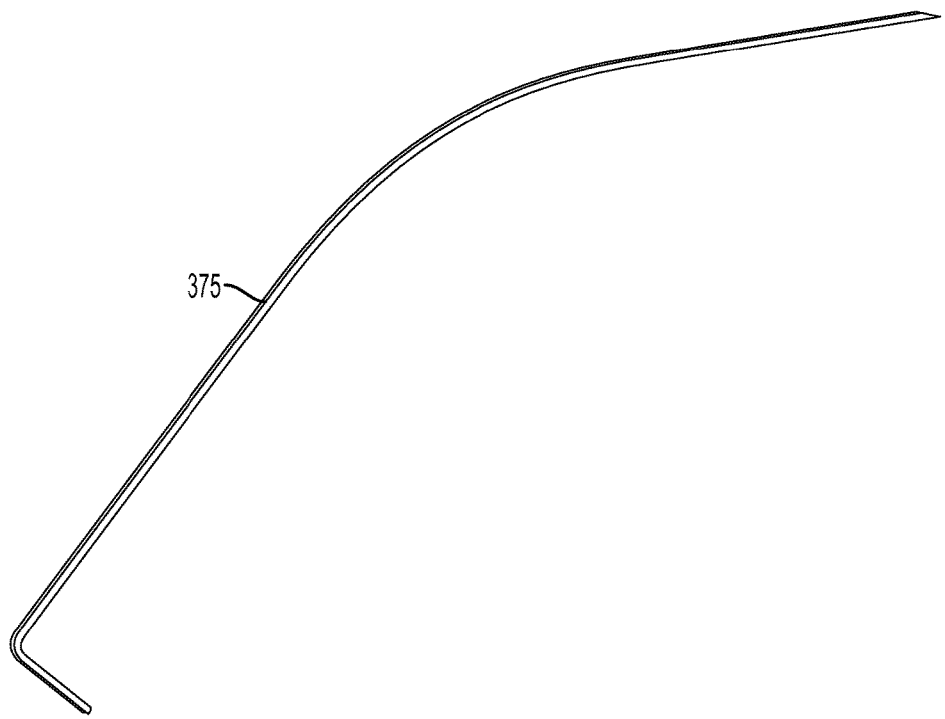
FIGS. 27 and 28 are views of a semi-circular trocar used with the D-lumen cannula in the fluid delivery device of FIGS. 18-23.
Figure 28:
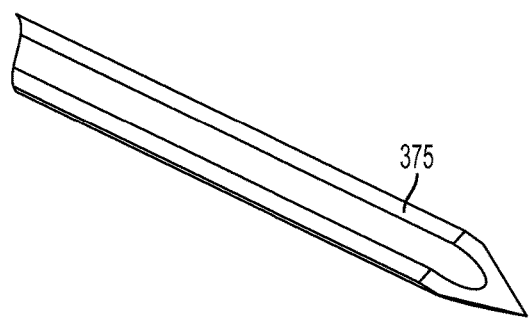
Figure 29:
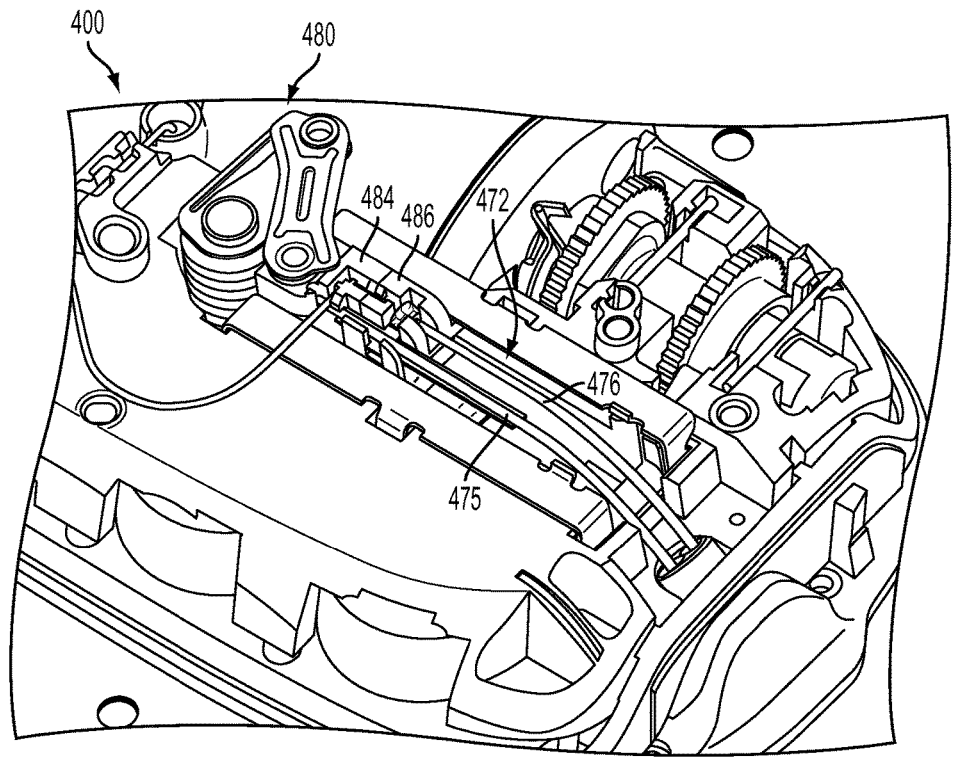
FIGS. 29-35 are views of another embodiment of a fluid delivery device including an oval trocar for inserting a monitor test strip transcutaneously.
Figure 30:
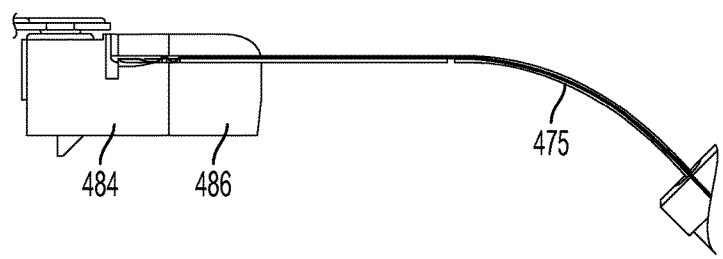
Figure 31:
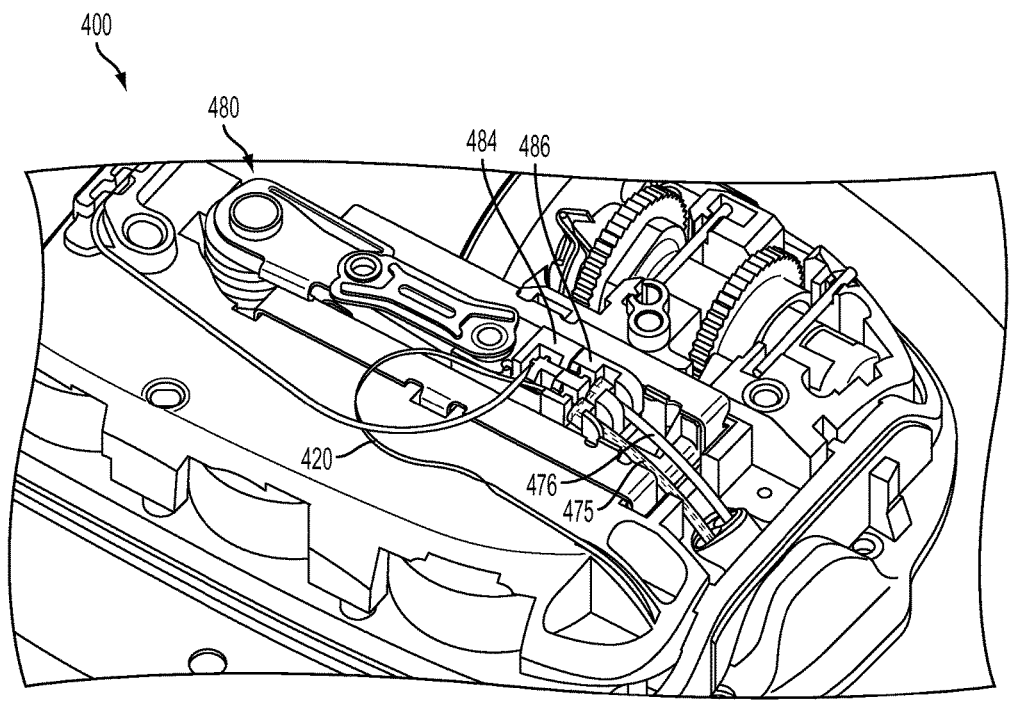
Figure 32:
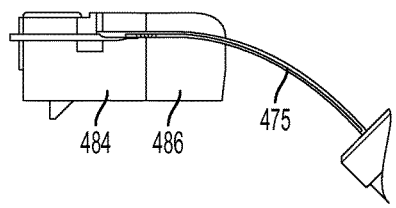
Figure 33:
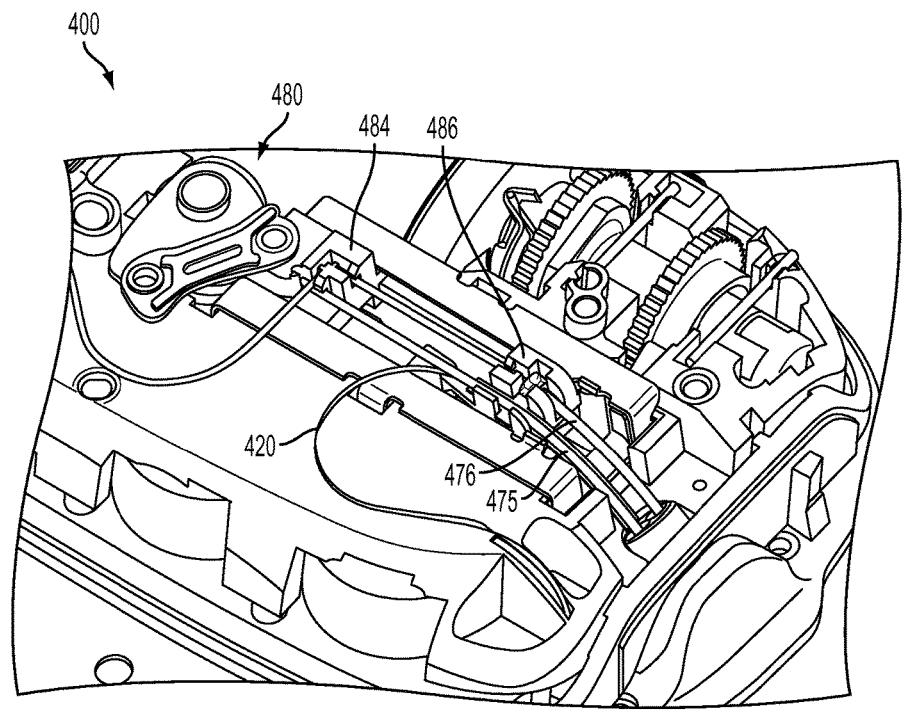
Figure 34:
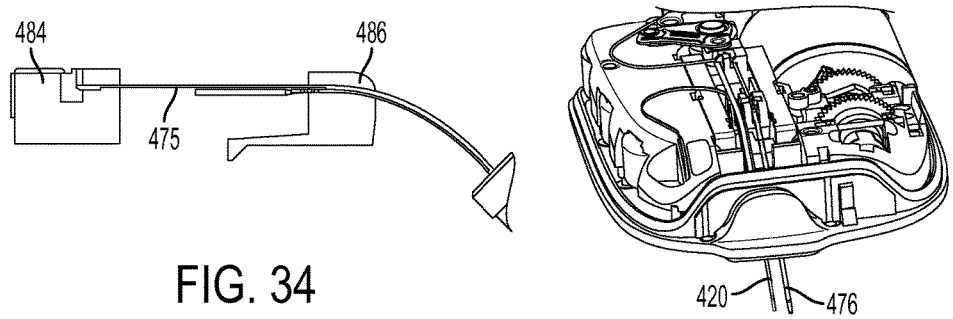

As shown in FIGS. 9 and 10, the cam finger 292 may also be used to lock the second sliding member 286 in the insertion position. A locking portion 288 of the second sliding member 286 engages a locking portion 293 of the cam finger 292 when the linkage mechanism 282 is fully extended in the intermediate position and prevents the second sliding member 286 from retracting such that the cannula remains inserted. As discussed above, the second sliding member 286 may also be locked by one or more latches (not shown) extending from a top of the frame 290.

According to one embodiment, as shown in FIGS. 11-17, the cannula 176 providing the transcutaneous access for delivery the fluid may also be used to introduce the monitor test strip 120. In this embodiment, the cannula 176 includes a first lumen 175 for receiving the needle/trocar 174 and a second lumen 177 for receiving the test strip 120. As shown, the first lumen 175 has a circular (cylindrical) profile and the second lumen 177 has a rectangular profile. The cannula 176 may also include one or more windows 179*a*, 179*b* providing access to one or more sensors 122*a*, 122*b* on the test strip 120. As shown, the plurality of windows 179*a*, 179*b* of the cannula 176 may be arranged on a same side of the sidewall of cannula 176, with the first window 179*a* arranged at a distance from the distal end tip of the cannula 176 which is less than the distance of the second window 179*b* from the distal end tip of the cannula 176.

To insert the test strip 120 into second lumen 177, the test strip 120 passes into second lumen 177 at the head 178 of the cannula 176 and extends to the window(s) 179*a*, 179*b*. Thus, at least one window 179*a*, 179*b* exposes a sensor 122*a*, 122*b* of the monitoring test strip 120. In the example embodiment, two windows 179*a*, 179*b* are provided with the window 179*a* closest to the tip of the cannula 176 providing access to the main sensor area and the window 179*b* farthest from the tip providing a reference. Although a specific shape and configuration of a bi-lumen cannula is shown, other configurations of a cannula with first and second lumens may also be used to both deliver a therapeutic fluid and introduce a test strip subcutaneously.

According to another embodiment, as shown in FIGS. 18-28, a fluid delivery device 300 may include a transcutaneous access tool 372 with a first cannula 376 for delivering fluid and a second cannula 377 for introducing a test strip 320. The first cannula 376 receives a first needle/trocar 374 (shown as a circular needle) to facilitate insertion of the first cannula 376 and the second cannula 377 receives a second needle/trocar 375 (shown as a semi-circular trocar) to facilitate insertion of the second cannula 377. The fluid deliver device 300 includes an insertion mechanism 380, similar to the first described embodiment above, but with sliding members 384, 386 coupled to both the needle 374 and the trocar 375 and both cannulas 376, 377. The insertion mechanism 380 inserts the second cannula 377 and the trocar 375 and then retracts the trocar 375 in the same manner as described above. The test strip 320 remains inserted after the trocar 375 is retracted. Thus, both the first needle/trocar 374 and the second needle/trocar 375 may be introduced into the patient simultaneously, particularly to reduce the pain of sequential insertions.

Similar to the above described embodiment, first cannula 376 includes a circular (cylindrical) lumen 376*a*. As shown in greater detail in FIGS. 24-26, the second cannula 377 includes a semi-circular (D-shaped) lumen 377*a* to allow the monitor strip to sit relatively flat within the cannula 377. The second cannula 377 also includes one or more windows 379*a*, 379*b* providing access to one or more sensors 320*a*, 320*b* on the test strip 320 (see FIGS. 21 and 23). As shown, similar to the prior embodiment, the plurality of windows 379*a*, 379*b*, of the cannula 377 may be arranged on a same side of the sidewall of the cannula 377, with the first window 379*a* arranged at a distance from the distal end tip of the cannula 377 which is less than the distance of the second window 379b from the distal end tip of the cannula 377. Thus, at least one window 379a, 379b exposes a sensor 320a, 320b of the monitoring test strip 320. In the example embodiment, two windows 379a, 379b are provided with the window 379a closest to the tip of the cannula 377 providing access to the main sensor area and the window 379b farthest from the tip providing a reference. As shown in greater detail in FIGS. 27 and 28, the trocar 375 has a shape corresponding to the D-shaped lumen 377a to allow the trocar 375 to be retracted leaving the test strip 320 inserted (see FIG. 23). As shown, the trocar includes a planar side surface 373 which corresponds to a planar test strip 320 such that, when assembled, the planar test strip 320 may be located adjacent the planar side surface 373 of the trocar 375 in the second cannula 377.

Figure 35:
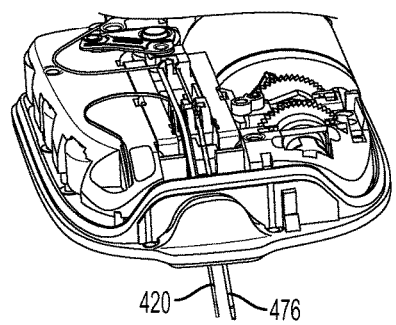

According to another embodiment, as shown in FIGS. 29-37, a fluid delivery device 400 may include a transcutaneous access tool 472 with a cannula 476 for delivering fluid and a needle or trocar 475 (shown as a semi-circular trocar) for introducing a test strip 420. The cannula 476 receives a needle/trocar 474 (shown as circular needle) to facilitate insertion of the cannula 476 and the trocar 475 is inserted with the test strip 420. The fluid deliver device 400 includes an insertion mechanism 480, similar to the first described embodiment above, but with sliding members 484, 486 coupled to both the needle 474 and the trocar 475. The insertion mechanism 480 inserts the trocar 475 (FIGS. 31 and 32) and then retracts the trocar 475 (FIGS. 33 and 34) in the same manner as the needle/trocar described above. The test strip 420 remains inserted after the trocar 475 is retracted (FIG. 35). In contrast to the prior embodiment, the needle/trocar 475 introduces the monitoring test strip 420 subcutaneously solely (i.e. without the monitoring test strip 420 being introduced with a cannula).

Figure 36:
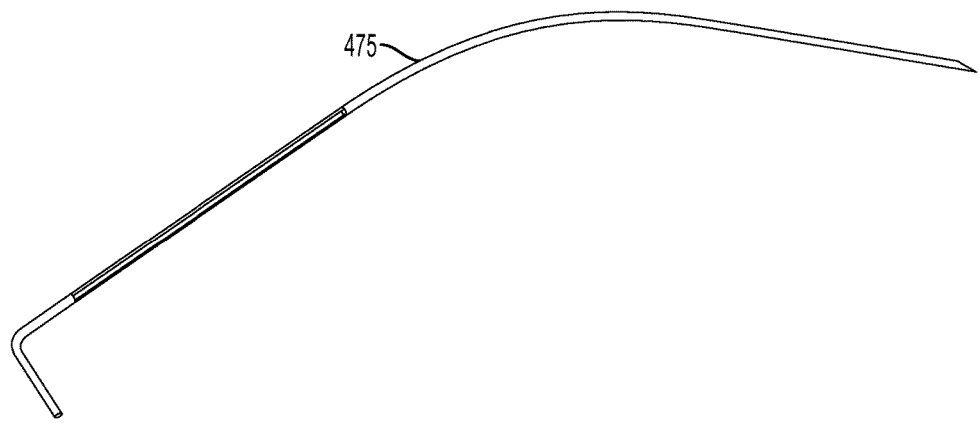
FIG. 36 is a side view of the oval trocar for use in the fluid delivery device shown in FIGS. 29-35.
Figure 37:
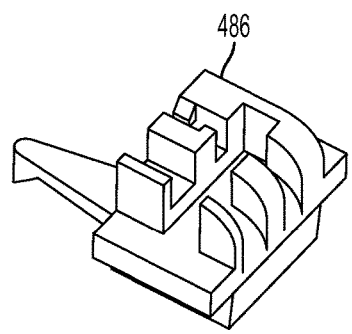
FIG. 37 is a top perspective view of a second sliding member for use in the fluid delivery device shown in FIGS. 29-35.

The trocar 475 is shown in greater detail in FIG. 36. The second sliding member 486 is shown in greater detail in FIG. 37. In this embodiment, the second sliding member 486 is designed to capture the cannula 476 and to receive and allow the trocar 475 to pass through.

Accordingly, various embodiments of the fluid delivery device may use the transcutaneous access tool both to deliver fluid and to introduce a test strip subcutaneously to provide integrated monitoring.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. An infusion device, the device comprising:
a housing, the housing containing a fluid reservoir, a monitoring test strip, a transcutaneous access tool, and a transcutaneous access tool insertion mechanism;
the fluid reservoir to contain a therapeutic fluid;
the transcutaneous access tool fluidly coupled to the fluid reservoir, the transcutaneous access tool configured to deliver the therapeutic fluid subcutaneously and the monitoring test strip subcutaneously;
the transcutaneous access tool including a cannula having a length, a first lumen and a second lumen, the first lumen having a longitudinal axis extending along the length of the cannula and the second lumen having a longitudinal axis extending along the length of the cannula, wherein the first lumen longitudinal axis and the second lumen longitudinal axis are different axes;
the first lumen of the cannula fluidly coupled with the fluid reservoir, and a deployable and retractable needle/trocar located within the first lumen;
the second lumen of the cannula containing the monitoring test strip;
the transcutaneous access tool insertion mechanism configured to extend and insert the cannula together with the needle/trocar subcutaneously upon deployment of the needle/trocar, and thereafter retract the needle/trocar within the cannula while the cannula remains inserted subcutaneously;
the transcutaneous access tool configured such that, when the therapeutic fluid from the fluid reservoir is delivered through the first lumen of the cannula, the needle/trocar including a distal end thereof is contained within the first lumen of the cannula;
the cannula together with the needle/trocar being extendable, and the needle/trocar being retractable, with energy stored in the transcutaneous access tool insertion mechanism.

2. The infusion device of claim 1 wherein the fluid reservoir comprises an insulin reservoir, and wherein the monitoring test strip comprises a continuous glucose monitoring test strip.

3. The infusion device of claim 1 wherein the energy stored in the transcutaneous access tool insertion mechanism is stored in a spring.

4. The infusion device of claim 1 wherein the transcutaneous access tool includes a cannula, a first needle/trocar passing through a lumen of the cannula, and a second needle/trocar configured to introduce the monitoring test strip subcutaneously.

5. The infusion device of claim 4 wherein the needle/trocar is configured to introduce the monitoring test strip subcutaneously solely without the monitoring test strip being introduced with a cannula.

6. The infusion device of claim 1 wherein the transcutaneous access tool includes first and second cannulas, a first needle/trocar passing through a lumen of the first cannula, and a second needle/trocar passing through a lumen of the second cannula, and wherein the monitoring test strip is located in the second cannula.

7. The infusion device of claim 6 wherein the second needle/trocar passing through a lumen of the second cannula is a trocar having a planar surface and the monitoring test strip comprises a planar strip, and wherein the planar strip is located adjacent the planar surface of the trocar in the second cannula.

8. The infusion device of claim 6 wherein the second cannula includes at least one window for exposing a sensor area on the monitoring test strip subcutaneously.

9. The infusion device of claim 8 wherein the at least one window of the cannula includes a plurality of windows, and wherein at least one window exposes a sensor of the monitoring test strip.

10. The infusion device of claim 8 wherein the plurality of windows of the cannula include a first window arranged at a first distance from a tip of the cannula and a second window arranged at a second distance from the tip of the cannula, wherein the first distance is less than the second distance.

11. The infusion device of claim 1 wherein the cannula includes at least one window for exposing a sensor area of the monitoring test strip subcutaneously.

12. The infusion device of claim 11 wherein the at least one window of the cannula includes a plurality of windows, and wherein at least one window exposes a sensor of the monitoring test strip.

13. The infusion device of claim 12 wherein the plurality of windows of the cannula include a first window arranged at a first distance from a tip of the cannula and a second window arranged at a second distance from the tip of the cannula, wherein the first distance is less than the second distance.

14. A method to treat diabetes mellitus comprising:
    providing an infusion device, the device comprising,
        a housing, the housing containing a fluid reservoir, a monitoring test strip, a transcutaneous access tool, and a transcutaneous access tool insertion mechanism;
        the fluid reservoir to contain a therapeutic fluid;
        the transcutaneous access tool fluidly coupled to the fluid reservoir, the transcutaneous access tool configured to deliver the therapeutic fluid subcutaneously and the monitoring test strip subcutaneously;
        the transcutaneous access tool including a cannula having a length, a first lumen and a second lumen, the first lumen having a longitudinal axis extending along the length of the cannula and the second lumen having a longitudinal axis extending along the length of the cannula, wherein the first lumen longitudinal axis and the second lumen longitudinal axis are different axes;
        the first lumen of the cannula fluidly coupled with the fluid reservoir, and a deployable and retractable needle/trocar located within the first lumen;
        the second lumen of the cannula containing the monitoring test strip;
        the transcutaneous access tool insertion mechanism configured to extend and insert the cannula together with the needle/trocar subcutaneously upon deployment of the needle/trocar and thereafter retract the needle/trocar within the cannula while the cannula remains inserted subcutaneously;
        the transcutaneous access tool configured such that, when the therapeutic fluid from the fluid reservoir is delivered through the first lumen of the cannula, the needle/trocar including a distal end thereof is contained within the first lumen of the cannula; and
        the cannula together with the needle/trocar being extendable, and the needle/trocar being retractable, with energy stored in the transcutaneous access tool insertion mechanism; and
    delivering the therapeutic fluid subcutaneously to a patient with the transcutaneous access tool, and introducing the monitoring test strip subcutaneously to the patient with the transcutaneous access tool.

15. The method of treating diabetes mellitus of claim 14 wherein:
    the transcutaneous access tool includes cannula, a first needle/trocar passing through a lumen of the cannula, and a second needle/trocar trocar including the monitoring test strip;
    inserting the first needle/trocar and the cannula subcutaneously into the patient, retracting the first needle/trocar from the patient and providing the therapeutic fluid through the lumen of the cannula to deliver the therapeutic fluid subcutaneously to a patient;
    inserting the second/needle trocar with the monitoring test strip subcutaneously into the patient to introduce the monitoring test strip subcutaneously to the patient.

16. The method of treating diabetes mellitus of claim 14 wherein the energy stored in the transcutaneous access tool insertion mechanism is stored in a spring.

17. The method of treating diabetes mellitus of claim 14 wherein:
    the monitoring test strip is located in a second lumen of the cannula, and further comprising
    inserting the needle/trocar and the cannula subcutaneously into the patient;
    retracting the needle/trocar from the patient; and
    providing the therapeutic fluid through the first lumen of the cannula to deliver the therapeutic fluid subcutaneously to a patient.

18. The method of treating diabetes mellitus of claim 17 wherein
    the cannula includes at least one window which exposes a sensor of the monitoring test strip to blood of the patient, and further comprising
    receiving data from the sensor concerning a glucose level of the patient, and
    determining an output of the therapeutic fluid from the reservoir based on the glucose level.

19. The method of treating diabetes mellitus of claim 14 wherein:
    the transcutaneous access tool includes first and second cannulas, a first needle/trocar passing through a lumen of the first cannula, and a second needle/trocar passing through a lumen of the second cannula, wherein the monitoring test strip is located in the second cannula and further comprising
    inserting the first needle/trocar and the first cannula subcutaneously into the patient, retracting the first needle/trocar from the patient and providing the therapeutic fluid through the lumen of the first cannula to deliver the therapeutic fluid subcutaneously to a patient;
    inserting the second needle/trocar, the monitoring test strip and the second cannula subcutaneously into the patient to introduce the monitoring test strip subcutaneously to the patient.

20. The method of treating diabetes mellitus of claim 19 wherein:
    the second cannula includes at least one window which exposes a sensor of the monitoring test strip to blood of the patient, and further comprising
    receiving data from the sensor concerning a glucose level of the patient, and
    determining an output of the therapeutic fluid from the reservoir based on the glucose level.

* * * * *